United States Patent [19]

Jagendorf et al.

[11] Patent Number: 5,674,992

[45] Date of Patent: Oct. 7, 1997

[54] CDNA ENCODING A RECA HOMOLOG IN EUKARYOTES

[75] Inventors: Andre Jagendorf, Ithaca, N.Y.; Heriberto Cerutti, Durham, N.C.

[73] Assignee: Cornell Research Foundation, Inc., Ithaca, N.Y.

[21] Appl. No.: 261,110

[22] Filed: Jun. 16, 1994

Related U.S. Application Data

[63] Continuation of Ser. No. 938,332, Aug. 28, 1992, abandoned.

[51] Int. Cl.⁶ ............................................. C12N 15/29
[52] U.S. Cl. ................................................... 536/23.6
[58] Field of Search .......................... 536/23.6; 530/370; 435/240.1, 240.2, 240.4, 243, 320.1

[56] References Cited

U.S. PATENT DOCUMENTS

| | | | |
|---|---|---|---|
| 4,713,337 | 12/1987 | Jasin et al. | 435/172.3 |
| 4,774,180 | 9/1988 | Toth et al. | 435/69.7 |
| 4,849,335 | 7/1989 | Hofnung et al. | 435/6 |
| 4,963,487 | 10/1990 | Schimmel | 435/172.3 |
| 5,087,564 | 2/1992 | Mai et al. | 435/69.7 |

FOREIGN PATENT DOCUMENTS

| | | |
|---|---|---|
| 0 063 522 | 10/1982 | European Pat. Off. . |
| WO 87/00203 | 1/1987 | WIPO . |
| WO 91/17267 | 11/1991 | WIPO . |

OTHER PUBLICATIONS

Murphy, R.C. et al., Journal of Bacteriology 172(2): 967–976 (1990).

*Primary Examiner*—Mindy Fleisher
*Assistant Examiner*—Terry A. McKelvey
*Attorney, Agent, or Firm*—Nixon, Hargrave, Devans & Doyle LLP

[57] ABSTRACT

A nucleotide and deduced amino acid sequence of a cDNA encoding the *Arabidopsis thaliana* RecA protein is disclosed.

2 Claims, 2 Drawing Sheets

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 1404 base pairs
        ( B ) TYPE: nucleic acid
        ( C ) STRANDEDNESS: single
        ( D ) TOPOLOGY: linear     ( i i ) MOLECULE TYPE: cDNA     ( x i ) SEQUENCE DESCRIPTION: SEQ ID NO:1:

```
GATTCACAGC  TAGTCTTGTC  TCTGAAGCTG  AATCCAAGCT  TCACTCCTCT  TTCTCCTCTC    60
TTCCCTTTCA  CTCCATGTTC  TTCTTTTTCG  CCGTCGCTCC  GGTTTTCTTC  TTGCTACTCC   120
CGCCGCCTCT  ATTCTCCGGT  TACCGTCTAC  GCCGCGAAGA  AACTCTCCCA  CAAAATCAGT   180
TCTGAATTCG  ATGACAGAAT  CAACGGCGCT  CTCTCTCCCG  ACGCTGATTC  CCGCTTCCTC   240
GACCGCCAAA  AGGCTTTAGA  GGCAGCTATG  AATGACATTA  ACAGTTCATT  TGGTAAAGGA   300
AGTGTAACAA  GATTGGGGAG  TGCTGGTGGA  GCATTAGTGG  AGACCTTTTC  GAGTGGTATT   360
TTGACTCTTG  ATCTTGCTTT  AGGTGGAGGC  CTACCAAAGG  GTCGGGTAGT  CGAAATATAT   420
GGACCAGAAA  GTAGTGGCAA  GACCACGCTA  GCACTCCATG  CTATTGCTGA  AGTGCAGAAG   480
CTTGGAGGCA  ATGCAATGCT  TGTTGATGCA  GAGCATGCCT  TTGATCCAGC  GTATTCTAAA   540
GCATTAGGTG  TTGATGTAGA  AAATTTGATA  GTGTGCCAGC  CAGATAATGG  CGAGATGGCT   600
TTAGAAACTG  CAGACCGTAT  GTGTCGCTCA  GGTGCGGTTG  ACCTTATATG  TGTTGATTCT   660
GTTTCAGCAC  TTACTCCACG  AGCTGAGATT  GAAGGTGAGA  TTGGAATGCA  GCAAATGGGT   720
TTGCAAGCTC  GTCTTATGAG  TCAAGCTCTT  CGTAAAATGT  CAGGAAACGC  CTCTAAAGCT   780
GGGTGTACTC  TTATTTTCCT  AAACCAAATA  AGATACAAGA  TTGGTGTGTA  CTATGGGAAT   840
CCAGAGGTGA  CTAGCGGAGG  AATTGCGTTA  AAGTTCTTCG  CGTCGGTCCG  TCTAGAAATT   900
CGTTCTGCTG  GGAAGATCAA  ATCTAGCAAA  GGGATGAAG   ATATTGGTCT  TCGGGCTCGT   960
GTAAGAGTGC  AGAAGAGCAA  GGTTTCAAGA  CCGTATAAGC  AAGCAGAGTT  TGAGATTATG  1020
TTTGGGGAAG  GAGTCAGTAA  ACTGGGATGC  GTTCTTGATT  GTGCTGAAAT  TATGGAAGTT  1080
GTGGTCAAGA  AAGGTTCCTG  GTACAGCTAC  GAAGACCAAA  GGCTCGGGCA  AGGAAGAGAG  1140
AAAGCACTGC  AGCACTTAAG  GGAAAACCCT  GCTCTTCAAG  ACGAAATTGA  GAAGAAAGTG  1200
AGATTGTTGA  TGTTAGATGG  AGAAGTTCAT  CGATCAACTC  CTTTGATGAG  CAGCAGCTCT  1260
TCCTCGGCTT  CACATCGCGA  AGAAGAAGAA  GAAGACTCGC  TTGACGATTT  CCAATGACAT  1320
```

```
AACACTTAAG CTTGAGACTT TCGGATCTAT GGATGTACAA CACTTGATTT TCTCTCATCA        1380

TGTTCACCTC TTGTTTCAAG TTTC                                               1404
```

( 2 ) INFORMATION FOR SEQ ID NO:2:

( i ) SEQUENCE CHARACTERISTICS:
        ( A ) LENGTH: 438 amino acids
        ( B ) TYPE: amino acid
        ( C ) STRANDEDNESS: Not Relevant
        ( D ) TOPOLOGY: linear     ( i i ) MOLECULE TYPE: protein     ( x i ) SEQUENCE DESCRIPTION: SEQ ID NO:2:

```
Asp  Ser  Gln  Leu  Val  Leu  Ser  Leu  Lys  Leu  Asn  Pro  Ser  Phe  Thr  Pro
 1              5                        10                       15

Leu  Ser  Pro  Leu  Phe  Pro  Phe  Thr  Pro  Cys  Ser  Ser  Phe  Ser  Pro  Ser
               20                       25                       30

Leu  Arg  Phe  Ser  Ser  Cys  Tyr  Ser  Arg  Arg  Leu  Tyr  Ser  Pro  Val  Thr
               35                       40                       45

Val  Tyr  Ala  Ala  Lys  Lys  Leu  Ser  His  Lys  Ile  Ser  Ser  Glu  Phe  Asp
          50                       55                       60

Asp  Arg  Ile  Asn  Gly  Ala  Leu  Ser  Pro  Asp  Ala  Asp  Ser  Arg  Phe  Leu
65                       70                       75                       80

Asp  Arg  Gln  Lys  Ala  Leu  Glu  Ala  Ala  Met  Asn  Asp  Ile  Asn  Ser  Ser
                    85                       90                       95

Phe  Gly  Lys  Gly  Ser  Val  Thr  Arg  Leu  Gly  Ser  Ala  Gly  Gly  Ala  Leu
               100                      105                      110

Val  Glu  Thr  Phe  Ser  Ser  Gly  Ile  Leu  Thr  Leu  Asp  Leu  Ala  Leu  Gly
               115                      120                      125

Gly  Gly  Leu  Pro  Lys  Gly  Arg  Val  Val  Glu  Ile  Tyr  Gly  Pro  Glu  Ser
     130                      135                      140

Ser  Gly  Lys  Thr  Thr  Leu  Ala  Leu  His  Ala  Ile  Ala  Glu  Val  Gln  Lys
145                      150                      155                      160

Leu  Gly  Gly  Asn  Ala  Met  Leu  Val  Asp  Ala  Glu  His  Ala  Phe  Asp  Pro
               165                      170                      175

Ala  Tyr  Ser  Lys  Ala  Leu  Gly  Val  Asp  Val  Glu  Asn  Leu  Ile  Val  Cys
               180                      185                      190

Gln  Pro  Asp  Asn  Gly  Glu  Met  Ala  Leu  Glu  Thr  Ala  Asp  Arg  Met  Cys
          195                      200                      205

Arg  Ser  Gly  Ala  Val  Asp  Leu  Ile  Cys  Val  Asp  Ser  Val  Ser  Ala  Leu
     210                      215                      220

Thr  Pro  Arg  Ala  Glu  Ile  Glu  Gly  Glu  Ile  Gly  Met  Gln  Gln  Met  Gly
225                      230                      235                      240

Leu  Gln  Ala  Arg  Leu  Met  Ser  Gln  Ala  Leu  Arg  Lys  Met  Ser  Gly  Asn
               245                      250                      255

Ala  Ser  Lys  Ala  Gly  Cys  Thr  Leu  Ile  Phe  Leu  Asn  Gln  Ile  Arg  Tyr
               260                      265                      270

Lys  Ile  Gly  Val  Tyr  Tyr  Gly  Asn  Pro  Glu  Val  Thr  Ser  Gly  Gly  Ile
               275                      280                      285

Ala  Leu  Lys  Phe  Phe  Ala  Ser  Val  Arg  Leu  Glu  Ile  Arg  Ser  Ala  Gly
     290                      295                      300

Lys  Ile  Lys  Ser  Ser  Lys  Gly  Asp  Glu  Asp  Ile  Gly  Leu  Arg  Ala  Arg
305                      310                      315                      320

Val  Arg  Val  Gln  Lys  Ser  Lys  Val  Ser  Arg  Pro  Tyr  Lys  Gln  Ala  Glu
                    325                      330                      335
```

|     |     |     |     |     |     |     |     |     |     |     |     |     |     |
| --- | --- | --- | --- | --- | --- | --- | --- | --- | --- | --- | --- | --- | --- |
| Phe | Glu | Ile | Met<br>340 | Phe | Gly | Glu | Gly<br>345 | Val | Ser | Lys | Leu | Gly<br>350 | Cys | Val | Leu |
| Asp | Cys | Ala<br>355 | Glu | Ile | Met | Glu<br>360 | Val | Val | Lys | Lys<br>365 | Gly | Ser | Trp | Tyr |
| Ser | Tyr<br>370 | Glu | Asp | Gln | Arg<br>375 | Leu | Gly | Gln | Gly | Arg<br>380 | Glu | Lys | Ala | Leu | Gln |
| His<br>385 | Leu | Arg | Glu | Asn | Pro<br>390 | Ala | Leu | Gln | Asp | Glu<br>395 | Ile | Glu | Lys | Lys | Val<br>400 |
| Arg | Leu | Leu | Met | Leu<br>405 | Asp | Gly | Glu | Val | His<br>410 | Arg | Ser | Thr | Pro | Leu<br>415 | Met |
| Ser | Ser | Ser | Ser<br>420 | Ser | Ser | Ala | Ser | His<br>425 | Arg | Glu | Glu | Glu | Glu<br>430 | Glu | Asp |
| Ser | Leu | Asp | Asp<br>435 | Phe | Gln |

(2) INFORMATION FOR SEQ ID NO:3:

(i) SEQUENCE CHARACTERISTICS:
        (A) LENGTH: 1167 base pairs
        (B) TYPE: nucleic acid
        (C) STRANDEDNESS: single
        (D) TOPOLOGY: linear     (ii) MOLECULE TYPE: cDNA     (xi) SEQUENCE DESCRIPTION: SEQ ID NO:3:

```
GCCGCGAAGA AACTCTCCCA CAAAATCAGT TCTGAATTCG ATGACAGAAT CAACGGCGCT      60
CTCTCTCCCG ACGCTGATTC CCGCTTCCTC GACCGCCAAA AGGCTTTAGA GGCAGCTATG     120
AATGACATTA ACAGTTCATT TGGTAAAGGA AGTGTAACAA GATTGGGGAG TGCTGGTGGA     180
GCATTAGTGG AGACCTTTTC GAGTGGTATT TTGACTCTTG ATCTTGCTTT AGGTGGAGGC     240
CTACCAAAGG GTCGGGTAGT CGAAATATAT GGACCAGAAA GTAGTGGCAA GACCACGCTA     300
GCACTCCATG CTATTGCTGA AGTGCAGAAG CTTGGAGGCA ATGCAATGCT TGTTGATGCA     360
GAGCATGCCT TTGATCCAGC GTATTCTAAA GCATTAGGTG TTGATGTAGA AAATTTGATA     420
GTGTGCCAGC CAGATAATGG CGAGATGGCT TTAGAAACTG CAGACCGTAT GTGTCGCTCA     480
GGTGCGGTTG ACCTTATATG TGTTGATTCT GTTTCAGCAC TTACTCCACG AGCTGAGATT     540
GAAGGTGAGA TTGGAATGCA GCAAATGGGT TTGCAAGCTC GTCTTATGAG TCAAGCTCTT     600
CGTAAAATGT CAGGAAACGC CTCTAAAGCT GGGTGTACTC TTATTTTCCT AAACCAAATA     660
AGATACAAGA TTGGTGTGTA CTATGGGAAT CCAGAGGTGA CTAGCGGAGG AATTGCGTTA     720
AAGTTCTTCG CGTCGGTCCG TCTAGAAATT CGTTCTGCTG GAAGATCAA ATCTAGCAAA     780
GGGGATGAAG ATATTGGTCT TCGGGCTCGT GTAAGAGTGC AGAAGAGCAA GGTTTCAAGA     840
CCGTATAAGC AAGCAGAGTT TGAGATTATG TTTGGGGAAG GAGTCAGTAA ACTGGGATGC     900
GTTCTTGATT GTGCTGAAAT TATGGAAGTT GTGGTCAAGA AAGGTTCCTG GTACAGCTAC     960
GAAGACCAAA GGCTCGGGCA AGGAAGAGAG AAAGCACTGC AGCACTTAAG GGAAAACCCT    1020
GCTCTTCAAG ACGAAATTGA GAAGAAAGTG AGATTGTTGA TGTTAGATGG AGAAGTTCAT    1080
CGATCAACTC CTTTGATGAG CAGCAGCTCT TCCTCGGCTT CACATCGCGA AGAAGAAGAA    1140
GAAGACTCGC TTGACGATTT CCAATGA                                         1167
```

(2) INFORMATION FOR SEQ ID NO:4:

(i) SEQUENCE CHARACTERISTICS:
        (A) LENGTH: 388 amino acids (B) TYPE: amino acid
(C) STRANDEDNESS: Not Relevant
(D) TOPOLOGY: linear (ii) MOLECULE TYPE: protein (xi) SEQUENCE DESCRIPTION: SEQ ID NO:4:

```
Ala  Ala  Lys  Lys  Leu  Ser  His  Lys  Ile  Ser  Ser  Glu  Phe  Asp  Asp  Arg
 1              5                   10                            15

Ile  Asn  Gly  Ala  Leu  Ser  Pro  Asp  Ala  Asp  Ser  Arg  Phe  Leu  Asp  Arg
              20                   25                            30

Gln  Lys  Ala  Leu  Glu  Ala  Ala  Met  Asn  Asp  Ile  Asn  Ser  Ser  Phe  Gly
         35                        40                       45

Lys  Gly  Ser  Val  Thr  Arg  Leu  Gly  Ser  Ala  Gly  Gly  Ala  Leu  Val  Glu
     50                   55                        60

Thr  Phe  Ser  Ser  Gly  Ile  Leu  Thr  Leu  Asp  Leu  Ala  Leu  Gly  Gly  Gly
 65                       70                   75                          80

Leu  Pro  Lys  Gly  Arg  Val  Val  Glu  Ile  Tyr  Gly  Pro  Glu  Ser  Ser  Gly
                    85                        90                      95

Lys  Thr  Thr  Leu  Ala  Leu  His  Ala  Ile  Ala  Glu  Val  Gln  Lys  Leu  Gly
              100                      105                     110

Gly  Asn  Ala  Met  Leu  Val  Asp  Ala  Glu  His  Ala  Phe  Asp  Pro  Ala  Tyr
              115                      120                     125

Ser  Lys  Ala  Leu  Gly  Val  Asp  Val  Glu  Asn  Leu  Ile  Val  Cys  Gln  Pro
     130                      135                      140

Asp  Asn  Gly  Glu  Met  Ala  Leu  Glu  Thr  Ala  Asp  Arg  Met  Cys  Arg  Ser
145                       150                      155                     160

Gly  Ala  Val  Asp  Leu  Ile  Cys  Val  Asp  Ser  Val  Ser  Ala  Leu  Thr  Pro
               165                      170                     175

Arg  Ala  Glu  Ile  Glu  Gly  Glu  Ile  Gly  Met  Gln  Gln  Met  Gly  Leu  Gln
               180                      185                     190

Ala  Arg  Leu  Met  Ser  Gln  Ala  Leu  Arg  Lys  Met  Ser  Gly  Asn  Ala  Ser
          195                      200                     205

Lys  Ala  Gly  Cys  Thr  Leu  Ile  Phe  Leu  Asn  Gln  Ile  Arg  Tyr  Lys  Ile
     210                      215                      220

Gly  Val  Tyr  Tyr  Gly  Asn  Pro  Glu  Val  Thr  Ser  Gly  Gly  Ile  Ala  Leu
225                       230                      235                     240

Lys  Phe  Phe  Ala  Ser  Val  Arg  Leu  Glu  Ile  Arg  Ser  Ala  Gly  Lys  Ile
               245                      250                     255

Lys  Ser  Ser  Lys  Gly  Asp  Glu  Asp  Ile  Gly  Leu  Arg  Ala  Arg  Val  Arg
               260                      265                     270

Val  Gln  Lys  Ser  Lys  Val  Ser  Arg  Pro  Tyr  Lys  Gln  Ala  Glu  Phe  Glu
          275                      280                     285

Ile  Met  Phe  Gly  Glu  Gly  Val  Ser  Lys  Leu  Gly  Cys  Val  Leu  Asp  Cys
     290                      295                     300

Ala  Glu  Ile  Met  Glu  Val  Val  Lys  Lys  Gly  Ser  Trp  Tyr  Ser  Tyr
305                       310                     315                     320

Glu  Asp  Gln  Arg  Leu  Gly  Gln  Gly  Arg  Glu  Lys  Ala  Leu  Gln  His  Leu
               325                      330                     335

Arg  Glu  Asn  Pro  Ala  Leu  Gln  Asp  Glu  Ile  Glu  Lys  Lys  Val  Arg  Leu
               340                      345                     350

Leu  Met  Leu  Asp  Gly  Glu  Val  His  Arg  Ser  Thr  Pro  Leu  Met  Ser  Ser
          355                      360                     365

Ser  Ser  Ser  Ser  Ala  Ser  His  Arg  Glu  Glu  Glu  Glu  Asp  Ser  Leu
     370                      375                     380
```

Asp Asp Phe Gln
385

(2) INFORMATION FOR SEQ ID NO:5:

(i) SEQUENCE CHARACTERISTICS:
      (A) LENGTH: 150 base pairs
      (B) TYPE: nucleic acid
      (C) STRANDEDNESS: single
      (D) TOPOLOGY: linear    (ii) MOLECULE TYPE: cDNA    (xi) SEQUENCE DESCRIPTION: SEQ ID NO:5:

```
GATTCACAGC TAGTCTTGTC TCTGAAGCTG AATCCAAGCT TCACTCCTCT TTCTCCTCTC      60
TTCCCTTTCA CTCCATGTTC TTCTTTTTCG CCGTCGCTCC GGTTTTCTTC TTGCTACTCC     120
CGCCGCCTCT ATTCTCCGGT TACCGTCTAC                                      150
```

(2) INFORMATION FOR SEQ ID NO:6:

(i) SEQUENCE CHARACTERISTICS:
      (A) LENGTH: 50 amino acids
      (B) TYPE: amino acid
      (C) STRANDEDNESS: Not Relevant
      (D) TOPOLOGY: linear    (ii) MOLECULE TYPE: peptide    (xi) SEQUENCE DESCRIPTION: SEQ ID NO:6:

```
Asp Ser Gln Leu Val Leu Ser Leu Lys Leu Asn Pro Ser Phe Thr Pro
1               5                   10                  15

Leu Ser Pro Leu Phe Pro Phe Thr Pro Cys Ser Ser Phe Ser Pro Ser
                20                  25                  30

Leu Arg Phe Ser Ser Cys Tyr Ser Arg Arg Leu Tyr Ser Pro Val Thr
            35                  40                  45

Val Tyr
    50
```

CDNA ENCODING A RECA HOMOLOG IN EUKARYOTES

CROSS REFERENCES TO RELATED APPLICATIONS

This application is a continuation of U.S. application Ser. No. 07/938,332, filed Aug. 28, 1992, now abandoned.

The observation of chloroplast DNA recombinants in somatic hybrids of higher plants [see *Proc. Natl. Acad. Sci., USA* 82:6960 (1985)], genetic studies of the inheritance of chloroplast markers in several crosses of *Chlamydomonas* [see Boynton, J. E., Gillham, N. W., Newman, S. M., & Harris, E. H. (1991) in Cell Organelles. Advances in Plant Gene Research, ed. Herrmann, R. (Springer-Verlag, Vienna) Vol 6, pp. 1–48], the integration of donor DNA by homologous recombination in chloroplasts of transformed *Chlamydomonas* [see *Proc. Natl. Acad. Sci., USA* 88:1721 (1991)], and extensive comparative analyses of chloroplast genome structure [see Curr. Genet. 13:343 (1988); *Annu. Rev. Genet* 19:325 (1985); TIGS 6:115 (1990)] all indicate that DNA recombination occurs in chloroplasts of both higher plants and green algae. The biochemistry of any recombinational mechanism in chloroplasts is completely unknown, however.

It has been argued that the primary biological role of recombination is the repair of DNA damage [see *Science* 229:1277 (1985)]. Exposure of *E. coli* to DNA damaging agents induces the SOS response, resulting in derepression of approximately 20 genes (including recA). The RecA protein is involved in multiple aspects of this response, namely, regulation of gone induction by promoting cleavage of the LexA repressor [See *Ann Rev. Biochem.* 54:425 (1985); Cell 29:11 (1982)], recombinational repair, SOS mutagenesis, DNA replication [see *Proc Natl. Acad. Sci. USA* 84:6805 (1987)] and duplication mutagenesis. In other organisms, genes involved in DNA repair/recombination are also induced in response to DNA damage [see *BioEssays* 12:295 (1991)].

It is generally accepted that plastids originated from cyanobacterial progenitors, acquired by an ancestral eukaryotic cell through an endosymbiotic event [see *J. Mol. Evol* 28:98 (1988); EMBOJ. 10:3073 (1991)]. Therefore we believed that any chloroplast recombination system should be related to an eubacterial counterpart.

In *E. coli*, and many other prokaryotes, the RecA protein, a 38 KDa protein essential for homologous DNA recombination and a variety of SOS responses to DNA damage [see *Biochimie* 73:289 (1991); *J. Moi. Biol.* 212:79 (1990); Mutat. Res. 236:301 (1990); *Crit Rev. Biochem. Mol. Biol.* 25:415 (1990); *J Bacteriol* 171:2415 (1989)]. It is the pairing reaction between homologous DNA sequences that ultimately leads to homologous recombinations which makes RecA protein useful for DNA diagnostics and therapeutic applications.

In addition to the preceding journal articles, a number of patents have recently issued which make reference to the recA gene or RecA protein. However, these patents are not relevant to the recA gene or Rec protein of higher plants as is the present invention.

U.S. Pat. No. 5,087,564, for example, describes a method to create fusion proteins in bacteria using the endogenous RecA, on the end of which oligopeptides or polypeptides are fused; collecting the expressed fusion protein; and removing the unwanted endogenous protein following making a split between them by a specific endopeptidase. However, this teaching has nothing to do with a higher plant recA gene, or nuclear DNA transformation in higher plants.

U.S. Pat. No. 4,849,335 deals with mutagen damage to DNA. In bacteria, damage to its DNA evokes an "SOS" response leading to the induction of enzymes that help repair damaged DNA. One of the crucial enzymes in this response, and one that is induced, is RecA. The goal of this patent is to enhance bacteria for production of increased amounts of either RecA or one of the other SOS proteins, following exposure to potentially mutagenic agents. However, this teaching has nothing to do with a higher plant recA gene, or nuclear DNA transformation in higher plants.

U.S. Pat. No. 4,774,180 describes a teaching aimed at constructing fusion proteins of several enzymes in a row, hoping that these might be more efficient for some industrial uses than having individual enzymes. Such a technique would certainly aid in the purification of the expressed enzymes since all of them could be isolated as a single package. As described, in order to achieve this goal, inactivation of the endogenous recA gene was necessary. However, this teaching has nothing to do with a higher plant recA gene, or nuclear DNA transformation in higher plants.

U.S. Pat. Nos. 4,713,337 and 4,963,487 describe a method to inactivate any desired gone in the bacterial chromosome, and requires the RecA protein to be present in the initial step, and then absent (either inactivated or deleted) for the second step. However, this teaching has nothing to do with a higher plant recA gene, or nuclear DNA transformation in higher plants.

European Published Patent Application 0 063 522 appears to describe a signal which inhibits cell division if DNA replication) is prevented or if the DNA is damaged. The inventors postulate that this signal activates the RecA protein to a form which aids LexA autodigest. Digestion of LexA leads to derepression of the genes involved in the SOS response, including massive synthesis of RecA itself. This technique is irrelevant to higher plant RecA protein since there is no evidence of any SOS response in higher plants similar to that found in bacteria; even if there were one, it cannot be initiated with the RecA protein according to the present invention interacting with a repressor of nuclear genes because the RecA protein of the present invention is found only inside of chloroplasts, far removed from the nucleus. Thus, this teaching has nothing to do with a higher plant recA gene, or nuclear DNA transformation in higher plants.

International Published Patent Application WO 87/00203 describes a technique for the overproduction of desired proteins in bacteria. This is accomplished by substituting the gene for the desired protein into the same place on a plasmid now occupied by the toxin, colicin. To be effective, the production of the desired protein needs to be induced by some environmental change, and it is suggested to use a strain of *E. coli* in which the recA gene protease function is inducible by high temperature. This teaching has nothing to do with a higher plant recA gene, or nuclear DNA transformation in higher plants.

International Published Patent Application WO 91/17267 describes a method for in vitro hybridization and amplification of DNA which utilizes the RecA protein from bacteria. While this is a defined use of bacterial RecA, it has nothing to do with a higher plant recA gene, or nuclear DNA transformation in higher plants.

In searching for a possible higher plant recA gene, in making the present invention, we used a cyanobacterial recA as a probe, and found homologous sequences in nuclear DNA from pea and *Arabidopsis thaliano*. With the same probe we have cloned an *Arabidopsis thaliana* cDNA that encodes a protein highly homologous to eubacterial RecA, except for a predicted chloroplast transit peptide at its amino terminus. The likely expressed protein was detected in chloroplast stromal extracts by cross-reaction with polyclonal antibodies to *E. coil* RecA protein.

Chloroplast DNA recombination has been studied extensively, particularly in Chlamydomonas by genetic analysis [see Theor. Appl. Genet. 79:17 (1990)]. There has been much work suggesting the involvement of certain sequence elements in plastid DNA recombination. However, up until the making of the present invention, very little was known at the enzymatic level. The finding of a plastid localized recA homlog, according to the teachings of the present invention, provides the first biochemical evidence for a chloroplast recombination system and strongly supports its relationship to the eubacterial counterpart. The present invention also provides the first observation of a recA homolog in any eukaryote. While recombination/repair enzymes have been identified in various other eukaryotes [see *J. Biol. Chem* 65:11108 (1990); *Cell* 29:367 (1982); *Proc. Natl. Acad. Sci. US* 85:5560 (1987); *Proc. Natl. Acad. Sci. US* 85;3683 (1988); *J. Biol. Chem.* 264:20568 (1989)], they have structures and enzymatic characteristics that differ from the bacterial RecA protein, A more thorough understanding of the present invention will be achieved after consideration of the following figures and examples. These figures and examples are provided to allow for a more complete understanding of the present invention, and are in no way intended to limit or otherwise define the exact terms of the present invention to the exclusion of equivalent or modified embodiments of the present invention.

BRIEF DESCRIPTION OF THE DRAWINGS

More specifically, and as will be more thoroughly discussed in the following examples and discussion, FIG. 1 shows a gel composite of three separate separations in which lane 1 contains a protoplast fraction; lane 2 contains a chloroplast fraction; lane 3 contains a chloroplast stromal fraction (half the amount of protein as loaded in lanes 1 and 2); and lane 4 contains a purified *E. coli* RecA protein. Separation "b" depicts mitomycin C induction in the steady state level of the chloroplast protein similar to *E. coli* RecA. This protein is slightly smaller in pea (38 kDa) than in Arabidopsis. In this separation, pea protoplasts were incubated for 12 hours in the presence of 0, 6, 15 or 30 µM mitomycin C (lanes 1 to 4, respectively), before protein isolation, Separation "c" depicts the same blot shown in "b" which was reprobed with antiserum to the γ subunit of the chloroplast ATP synthetase, a nuclear encoded chloroplast protein similar in size to RecA. This protein Was not induced by DNA damaging agents and served as a control for the proper loading of the lanes. In FIG. 2, lanes 1 and 2 contained total Arabidopsis DNA (1 ug); lane 3 contained total pea DNA (8 ug); lane 4 contained pea chloroplast DNA (1 ug). Restriction enzymes used included Hind ("H") and PstI ("P"). A further explanation and importance of these gels are described in the discussion of the data obtained from the following examples.

The following example I depicts the isolation of stroma from intact chloroplasts and the immunodetection of a RecA protein in accordance with the present invention:

EXAMPLE I

Protoplasts were prepared from leaves of Arabidopsis or pea by digestion with 3% (w/v) Cellulysin (Calbiochem) and 0.5% (w/v) Macerase (Calbiochem) according to the following protocol:

Pea seedlings (cv. Progress No. 9) were grown on a 12 hr day in growth chambers, in vermiculite, for 9 to 12 days. Unfolded, but not fully expanded leaves (1 g fresh weight) were surface sterilized With NaOCl, cut into strips, and placed into 9 cm Petri dishes with 10 ml of buffer A (20 mM MES, pH 5.8; 350 mM sorbitol; 1 mM $KH_2PO_4$; 5 mM $MgCl_2$; 30 mM $CaCl_2$; 1 mM DTT; 1% BSA) containing 3% Cellulysin and 0.5% Macerase. The dishes were incubated for 4–5 hr at room temperature, in the dark, with shaking at 40 rpm for the final hour.

Protoplasts were isolated by filtration through 100 µm nylon mesh followed by centrifugation (5 min, 75 g). The pellet was resuspended in buffer B (50 mM Tricine: pH 7.0; 380 mM sucrose; 20 mM $CaCl_2$; 0.5% BSA; 25% Percol), and overlaid with buffer C (buffer B without Percoll) and buffer D (buffer C with 380 mM sorbitol in lieu of sucrose). After centrifugation (12 min, 370 g), intact protoplasts were collected at the interface between buffers C and D, and washed once (5 min, 75 g) with either chloroplast isolation buffer [see Methods in Enzymology 118:282 (1986)], for cell fractionation, or culture medium [see In Vitro Cell Der Biol 25:571 (1989)], for treatment with DNA damaging agents. Finally, protoplasts were resuspended in the same solutions, counted, and adjusted to the desired density, Chloroplasts were broken by osmotic lysis in which intact chloroplasts (300 µl) were sedimented in an Eppendorf microcentrifuge for 2 minutes. The supernatant was discarded, and the chloroplasts resuspended by vortex mixing with 10 mM Na-pyrophysphate to cause osmotic breakage; thylakoid membranes removed by centrifugation.

The supernatant from the osmotic lysis was concentrated by acetone precipitation to give the chloroplast stromal fraction according to the following procedure:

A supernatant solution (as after centrifuging the osmotic lysate) was put into a fresh tube, and to it was added 4 volumes of –20° C. acetone. The tubes were vortexed, and kept on ice for 20 or more minutes. The tubes were then centrifuged for 7 min in an Eppendorf centrifuge (10,000 ×g); the supernatant removed, and the proteins redissolved in buffer containing 2% sodium dodecyl sulfate, 50 mM Tris pH 8.5, 50 mM dithiothreitol, 2% lithium dodecyl sulfate and 12% (w/v) sucrose. These were then ready for analysis by electrophoresis on acrylamide gels.

Potential bacterial contamination was tested by plating aliquots of isolated protoplasts or chloroplasts on LB medium [see Sambrook, J., Fritsch, E. F. & Maniatis, T. (1989) *Molecular Cloning: A Laboratory Manual*]. Proteins from different fractions were separated by 12% SDS-polyacrylamide gel electrophoresis, and electroblotted onto nitrocellulose [see *Proc. Natl. Acad. Sci. USA* 76:4350 (1979)] and probed With two polyclonal rabbit antisera to RecA protein from *E. coli* strain K12. The efficiency of transfer was determined by staining the filters with Ponceau S. The filter was treated with 5% non-fat dry milk in TBS (50 mM TRIS-HCl, pH 7.4; 200 mM NaCl) for 1 hr at room temperature, to fill up any spot on the filter without any protein on it with casein. RecA antiserum was added in the same solution as above at 1:2000 dilution and incubated overnight. After three 15 min washes with TBS (at least one containing Tween 20), the filters were blocked as before and incubated with a 1:2000 dilution of commercially available goat antibodies against rabbit IgG. The goat anti-rabbit IgG antibodies had been covalently bound to horseradish peroxidase. These were incubated with the nitrocellulose sheet for 2–3 hr at room temperature.

The nitrocellulose sheets were then washed three times with 5% non-fat dry milk in TBS, and three times with TBS (at least once with TBS containing 0.1% Tween 20). A chemiluminescent substrate (Amersham) was used for the autoradiographic detection. The nitrocellulose sheets, with horseradish peroxidase bound only where the original rabbit antibody, then the goat antibody had been bound, were mixed with the 2 components of the peroxidase detection kit for 1 minute, as in the manufacturer's directions. The action of peroxidase on the peroxidase +peroxidase substrate combination leads to a chemical reaction so energetic that it releases light for about 2 hrs. The nitrocellulose filter, with a few glowing spots, was placed next to a piece of X-ray film in the dark. After variable lengths of time, the X-ray film was removed from the filter and developed. Relative protein amounts were determined by densiometric scanning (Universal Imaging, Inc.) of the film images.

In some cases, the enzyme was inactivated by incubation in $H_2O_2$ and the blot reprobed with an antibody against the γ subunit of CF1.

The techniques for probing with polyclonal antisera are further described in *Proc. Natl. Acad. Sci. USA* 76:4350 (1979) and Harlow, E. and D. Lane, Antibodies—A Laboratory Manual, Cold Spring Harbor Laboratory Press, Cold Spring, N.Y.(1988).

Figure 1:
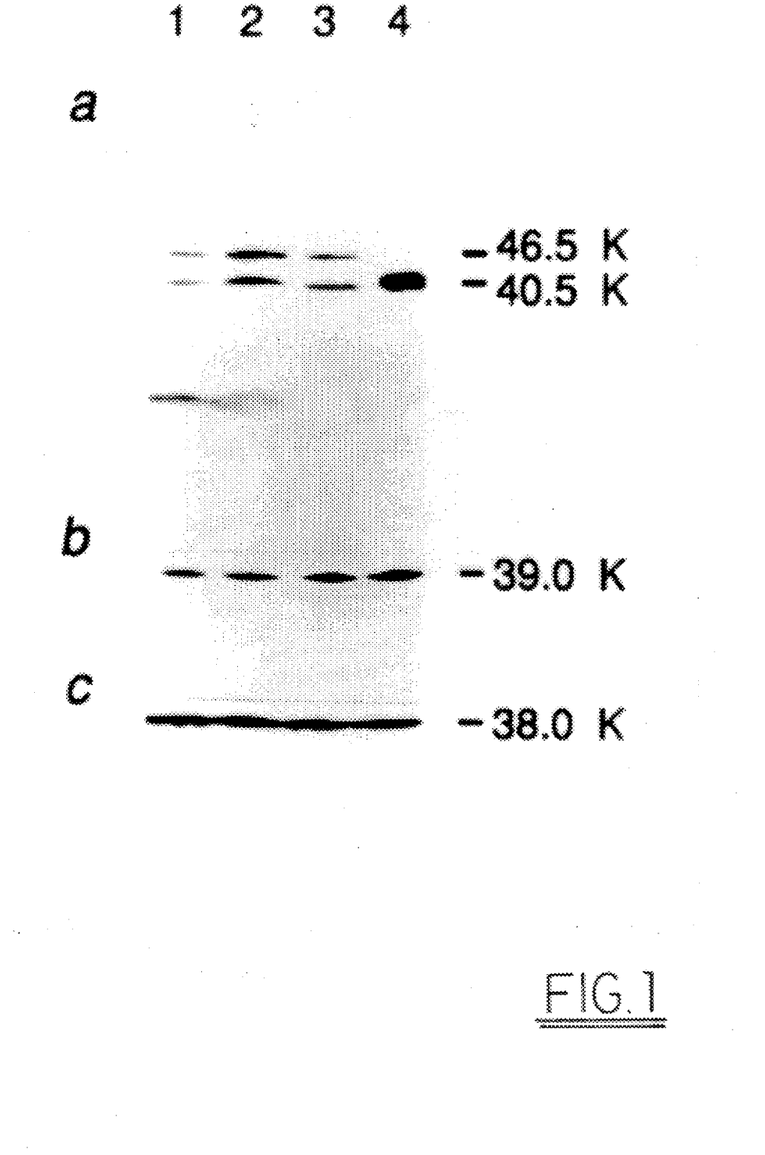
FIG. 1 depicts the detection of proteins immunologically related to *E. coli* RecA in *Arabidopsis thaliana.

The results from Example 1 were used to study the detection of a protein in chloroplast stroma immunologically related to *E. coli* RecA. An immunoblotting technique Was used to detect Arabidopsis proteins related to RecA (see FIG. 1, "a"). Although the data is not depicted in the figures, preimmune serum did not reveal any bands, however, two polyclonal antibodies raised against *E. coli* RecA cross reacted with three protoplast proteins. Two of them are soluble chloroplast proteins detected in the stromal fraction (see FIG. 1, "a"). The apparent molecular mass (Mr) of the faster moving stromal protein as 40.5 kDa, almost identical With that of *E. coli* RecA. Similar proteins were also identified in pea chloroplasts (see FIG. 1, "b"). Consistent with the presence of RecA in chloroplasts, DNA strand exchange, an essential activity of *E. coli* RecA, in crude stromal extracts from pea was also detected.

The following example II depicts the isolation of DNA and probing with a cyanobacterial recA gene fragment in accordance with the present invention.

EXAMPLE II

Total DNA was isolated from Arabidopsis leaves by a miniprep procedure. Isopycnic CsCl centrifugation was used for the purification of total DNA from pea leaves, and of chloroplast DNA from intact pea chloroplasts. Standard procedures were used for digestion, electrophoretic separation, and transfer of the DNA to nylon membranes. The filters were probed with a [$^{32}$P] labelled Bst EII fragment, comprising the 5' half of the coding sequence [see *J. Bacteriol.* 172:967 (1990)]. Prehybridization was at 70° C. for 6 hours and hybridization overnight at 60° C. [see *Proc. Natl. Acad. Sci. USA* 81:1991 (1984)]. Filters were washed 3 times for 1.5 hours with 2×SSC/0.1% SDS at room temperature, then 3 times in 0.2 x SSC/0.1% SDS at 50° C. for another 1.5 hours. The membranes were exposed to Kodak XAR-5 film with an intensifying screen.

The following example III depicts the cDNA cloning and sequencing in accordance with the present invention.

EXAMPLE III

A cDNA was isolated by screening approximately 300,000 members of an Arabidopsis library in the "lambda-YES" vector [see *Proc. Natl. Acad. Sci USA* 88:1731(1991)], using as probe the *Synechococcus recA* gene. The bacteriophages were plated [see *Molecular Cloning—A Laboratory Manual* (2nd ed), Cold Spring Harbor Laboratory, Cold Spring Harbor, N.Y. (1989)] on an *E. coli* strain deleted for recA in order to avoid confusion with the inserted plant recA gene (since both would have been detected by the labeled probe) [see *Genetics* 93:321 (1979)]. Standard procedures were used for library screening. After sub-cloning into Bluescript (Stratagene), nested deletions were generated and the DNA sequenced on both strands by the dideoxy chain termination method using T7 DNA polymerase. The sequences were analyzed with the Genetics Computer Group software package [see *Nucleic Acids Res.* 12:387 (1984)].

Figure 2:
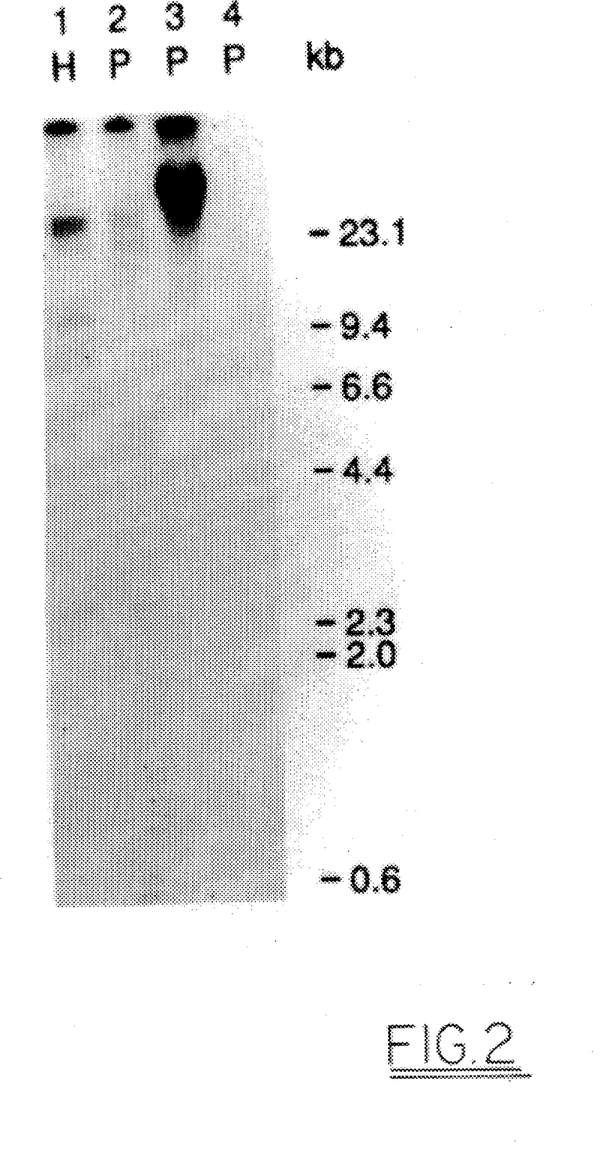
* and FIG. 2 depicts the southern blot showing sequences related to *Synechococcus recA* in genomio DNA from Arabidopsis and pea.

Genomic hybridization revealed sequences homologous to the *Synechococcus recA* gene in pea and Arabidopsis (see FIG. 2). However, any hybridization to purified chloroplast (see FIG. 2) or mitochondrial DNA was unable to be detected. Homology to recA has not been found in the completely sequenced chloroplast genomes of tobacco [see *EMBO J* 5:2043 (1986)], Marchantia [See *Nature* 322:572 (1986)], or rice [see *Mol. Gen. Genet.* 217:185 (1989)]. Moreover, induction of the stromai protein was prevented by protein synthesis inhibitors acting on cytosolic (80 S) ribosomes, also suggesting a nuclear localization for this gene.

Using the *Synechococcus recA* gene as a probe, an Arabidopsis cDNA library was screened in accordance with the present invention utilizing conventional techniques. A gene showing extensive homology to eubacterial recA was cloned in accordance with the present invention. The cloned cDNA was sequenced by standard techniques. Polymerase chain reaction analysis showed that this was the longest cDNA in the library encoding the RecA protein. This was accomplished with the aid of PCR methodology which can amplify DNA sequences based upon recognition of 2 separate sites by specific primers. For the right (3') end primer, a primer was selected which was homologous to an internal stretch of the gene, not too far from the 5' (left) end. The primer for the 3' end of the piece to be amplified was chosen to be homologous to a part of the vector which was carrying the gene. The formation of new DNA, homologous to this template, would thus include the 5' end of the gene itself.

This procedure was applied to the entire cDNA library as a template. A fairly large number of amplification products were selected and electrophoresed. By using radioactive nucleotides, the amplified clones could be detected by autoradiography. If there had been a cDNA in the library more complete at the 5' end than the one originally discovered, it should have appeared as a longer fragment of DNA. Sequencing of the longest one located showed it to be identical to the only originally isolated; there was no detectable clone any longer.

Although the cDNA is truncated at its 5' end, it is long enough to reveal the features of the encoded protein.

The following are the nucleotide and deduced amino acid sequences of a cDNA encoding the *Arabidopsis thaliana* RecA protein in accordance with the present invention. The nucleotide sequence is SEQ ID NO:1:

| | | | | | | | | | | | | | |
|---|---|---|---|---|---|---|---|---|---|---|---|---|---|
| GAT | TCA | CAG | CTA | GTC | TTG | TCT | CTG | AAG | CTG | AAT | CCA | AGC | 39 |
| TTC | ACT | CCT | CTT | TCT | CCT | CTC | TTC | CCT | TTC | ACT | CCA | TGT | 78 |
| TCT | TCT | TTT | TCG | CCG | TCG | CTC | CGG | TTT | TCT | TCT | TGC | TAC | 117 |
| TCC | CGC | CGC | CTC | TAT | TCT | CCG | GTT | ACC | GTC | TAC | GCC | GCG | 156 |
| AAG | AAA | CTC | TCC | CAC | AAA | ATC | AGT | TCT | GAA | TTC | GAT | GAC | 195 |
| AGA | ATC | AAC | GGC | GCT | CTC | TCT | CCC | GAC | GCT | GAT | TCC | CGC | 234 |
| TTC | CTC | GAC | CGC | CAA | AAG | GCT | TTA | GAG | GCA | GCT | ATG | AAT | 273 |
| GAC | ATT | AAC | AGT | TCA | TTT | GGT | AAA | GGA | AGT | GTA | ACA | AGA | 312 |
| TTG | GGG | AGT | GCT | GGT | GGA | GCA | TTA | GTG | GAG | ACC | TTT | TCG | 351 |
| AGT | GGT | ATT | TTG | ACT | CTT | GAT | CTT | GCT | TTA | GGT | GGA | GGC | 390 |
| CTA | CCA | AAG | GGT | CGG | GTA | GTC | GAA | ATA | TAT | GGA | CCA | GAA | 429 |
| AGT | AGT | GGC | AAG | ACC | ACG | CTA | GCA | CTC | CAT | GCT | ATT | GCT | 468 |
| GAA | GTG | CAG | AAG | CTT | GGA | GGC | AAT | GCA | ATG | CTT | GTT | GAT | 507 |
| GCA | GAG | CAT | GCC | TTT | GAT | CCA | GCG | TAT | TCT | AAA | GCA | TTA | 546 |
| GGT | GTT | GAT | GTA | GAA | AAT | TTG | ATA | GTG | TGC | CAG | CCA | GAT | 585 |
| AAT | GGC | GAG | ATG | GCT | TTA | GAA | ACT | GCA | GAC | CGT | ATG | TGT | 624 |
| CGC | TCA | GGT | GCG | GTT | GAC | CTT | ATA | TGT | GTT | GAT | TCT | GTT | 663 |
| TCA | GCA | CTT | ACT | CCA | CGA | GCT | GAG | ATT | GAA | GGT | GAG | ATT | 702 |
| GGA | ATG | CAG | CAA | ATG | GGT | TTG | CAA | GCT | CGT | CTT | ATG | AGT | 741 |
| CAA | GCT | CTT | CGT | AAA | ATG | TCA | GGA | AAC | GCC | TCT | AAA | GCT | 780 |
| GGG | TGT | ACT | CTT | ATT | TTC | CTA | AAC | CAA | ATA | AGA | TAC | AAG | 819 |
| ATT | GGT | GTG | TAC | TAT | GGG | AAT | CCA | GAG | GTG | ACT | AGC | GGA | 858 |
| GGA | ATT | GCG | TTA | AAG | TTC | TTC | GCG | TCG | GTC | CGT | CTA | GAA | 897 |
| ATT | CGT | TCT | GCT | GGG | AAG | ATC | AAA | TCT | TGC | AAA | GGG | GAT | 936 |
| GAA | GAT | ATT | GGT | CTT | CGG | GCT | CGT | GTA | AGA | GTG | CAG | AAG | 975 |
| AGC | AAG | GTT | TCA | AGA | CCG | TAT | AAG | CAA | GCA | GAG | TTT | GAG | 1014 |
| ATT | ATG | TTT | GGG | GAA | GGA | GTC | AGT | AAA | CTG | GGA | TGC | GTT | 1053 |
| CTT | GAT | TGT | GCT | GAA | ATT | ATG | GAA | GTT | GTG | GTC | AAG | AAA | 1092 |
| GGT | TCC | TGG | TAC | AGC | TAC | GAA | GAC | CAA | AGG | CTC | GGG | CAA | 1131 |
| GGA | AGA | GAG | AAA | GCA | CTG | CAG | CAC | TTA | AGG | GAA | AAC | CCT | 1170 |
| GCT | CTT | CAA | GAC | GAA | ATT | GAG | AAG | AAA | GTG | AGA | TTG | TTG | 1209 |
| ATG | TTA | GAT | GGA | GAA | GTT | CAT | CGA | TCA | ACT | CCT | TTG | ATG | 1248 |
| AGC | AGC | AGC | TCT | TCC | TCG | GCT | TCA | CAT | CGC | GAA | GAA | GAA | 1287 |
| GAA | GAA | GAC | TCG | CTT | GAC | GAT | TTC | CAA | TGA | 1317 | | | |
| CATAACACTT | AAGCTTGAGA | CTTTCGGATC | TATGGATGTA | 1357 | | | | | | | | | |
| CAACACTTGA | TTTTCTCTCA | TCATGTTCAC | CTCTTGTTTC | 1397 | | | | | | | | | |
| AAGTTTC | 1404 | | | | | | | | | | | | |

This sequence depicts a truncated cDNA containing a continuous open reading frame starting at it 5' end. The stop codon (TGA at 1315–1317) is followed by sequences with 75 to 80% homology to elements implicated in efficient polyadenylation of plant mRNAs [see Mogen, B. D., MacDonald, M. H., Graybosch, R., & Hurt, A. G. (1990) *The Plant Cell* 2:1261–1272].

The deduced areinc acid sequence for this peptide is as follows: SEQ ID NO:2:

Asp Ser Gln Leu Val Leu Ser Leu Lys Leu Asn Pro Ser Phe Thr
            5               10             15

Pro Leu Ser Pro Leu Phe Pro Phe Thr Pro Cys Ser Ser Phe Ser
        20              25             30

Pro Ser Leu Arg Phe Ser Ser Cys Tyr Ser Arg Arg Leu Tyr Ser
        35              40             45

Pro Val Thr Val Tyr Ala Ala Lys Lys Leu Ser His Lys Ile Ser
        50              55             60

Ser Glu Phe Asp Asp Arg Ile Asn Gly Ala Leu Ser Pro Asp Ala
        65              70             75

Asp Ser Arg Phe Leu Asp Arg Gln Lys Ala Leu Glu Ala Ala Met
        80              85             90

Asn Asp Ile Asn Ser Ser Phe Gly Lys Gly Ser Val Thr Arg Leu
        95             100           105

Gly Ser Ala Gly Gly Ala Leu Val Glu Thr Phe Ser Ser Gly Ile
        110           115           120

Leu Thr Leu Asp Leu Ala Leu Gly Gly Gly Leu Pro Lys Gly Arg
        125           130           135

-continued

Val Val Glu Ile Tyr Gly Pro Glu Ser Ser Gly Lys Thr Thr Leu
        140           145           150

Ala Leu His Ala Ile Ala Glu Val Gln Lys Leu Gly Gly Asn Ala
        155           160           165

Met Leu Val Asp Ala Glu His Ala Phe Asp Pro Ala Tyr Ser Lys
        170           175           180

Ala Leu Gly Val Asp Val Glu Asn Leu Ile Val Cys Gln Pro Asp
        185           190           195

Asn Gly Glu Met Ala Leu Glu Thr Ala Asp Arg Met Cys Arg Ser
        200           205           210

Gly Ala Val Asp Leu Ile Cys Val Asp Ser Val Ser Ala Leu Thr
        215           220           225

Pro Arg Ala Glu Ile Glu Gly Glu Ile Gly Met Gln Gln Met Gly
        230           235           240

Leu Gln Ala Arg Leu Met Ser Gln Ala Leu Arg Lys Met Ser Gly
        245           250           255

Asn Ala Ser Lys Ala Gly Cys Thr Leu Ile Phe Leu Asn Gln Ile
        260           265           270

Arg Tyr Lys Ile Gly Val Tyr Tyr Gly Asn Pro Glu Val Thr Ser
        275           280           285

Gly Gly Ile Ala Leu Lys Phe Phe Ala Ser Val Arg Leu Glu Ile
        290           295           300

Arg Ser Ala Gly Lys Ile Lys Ser Ser Lys Gly Asp Glu Asp Ile
        305           310           315

Gly Leu Arg Ala Arg Val Arg Val Gln Lys Ser Lys Val Ser Arg
        320           325           330

-continued

```
Pro Tyr Lys Gln Ala Glu Phe Glu Ile Met Phe Gly Glu Gly Val
            335             340                 345

Ser Lys Leu Gly Cys Val Leu Asp Cys Ala Glu Ile Met Glu Val
            350             355                 360

Val Val Lys Lys Gly Ser Trp Tyr Ser Tyr Glu Asp Gln Arg Leu
            365             370                 375

Gly Gln Gly Arg Glu Lys Ala Leu Gln His Leu Arg Glu Asn Pro
            380             385                 390

Ala Leu Gln Asp Glu Ile Glu Lys Lys Val Arg Leu Leu Met Leu
            395             400                 405

Asp Gly Glu Val His Arg Ser Thr Pro Leu Met Ser Ser Ser Ser
            410             415                 420

Ser Ser Ala Ser His Arg Glu Glu Glu Glu Asp Ser Leu Asp
            425             430                 435

Asp Phe Gln
```

The areinc acid sequence contains a putative chloroplast transit peptide (residues 1 to 51, inclusive of SEQ ID NO:2; the transit peptide has a nucleotide sequence as shown in SEQ ID NO:5 and an amino acid sequence as shown in SEQ ID NO:6) with a perfect consensus cleavage site (Val Tyr Ala Ala) located at residues 49 to 52, inclusive of SEQ ID NO:2. The predicted start of the mature protein begins with the alanine residue at position 51 of SEQ ID NO:2.

The amino terminus showing no similarity to bacterial RecA sequences is, as stated above, believed to be a chloroplast transit peptide. Chloroplast transit peptides are not highly homologous, except for a loosely conserved motif at the cleavage site for the stromal processing protease [see Eur. J. Biochem 180:535 (1989); FEBS Lett. 261:455 (1990)]. The deduced amino acid sequence contains a perfect match to this consensus cleavage site. When such a match is found, it is predicted to specify the correct cleavage site with 90% probability. The sequence upstream of the putative cleavage site is enriched for serine and threonine (29.5%), and is almost devoid of acidic residues (2.0%). It also lacks predicted secondary structures except for two relatively small regions, one of them an amphophilic β-strand next to the cleavage site. These are typical features of chloroplast transit peptides [see FEBS Lett. 278:1 (1991)], and strongly support that identity for the first 51 amino acids of the truncated sequence, The mature protein is predicted to be 387 amine acids long, with an amino acid sequence as shown in SEQ ID NO:4 and being encoded by the nucleotide sequence as shown in SEQ ID NO: 3 (residue 51 to residue 438 of SEQ ID NO:2 represent the amino acid sequence of the mature protein), with a calculated molecular mass of 41.8 kDa. This is close to the Mr of the faster moving protein identified in the chromoplast stromal fraction. The amine acid sequence of the peptide according to the present invention, specifically for Arabidopsis thaliana shows a 60.7% overall identity with the Synechococcus sp. protein, and 52–57% identity with 20 other prokaryotic RecA proteins, 10 of which are shown in the following table:

TABLE 1

Comparison Of The Amino Acid Sequences of Arabidopsis RecA and Several Eubacterial Homologs

| organism | percentage homology |
|---|---|
| Arabidopsis thaliana | 100.0 |
| Synechococcus sp | 60.7 |
| Anabaena variabilis | 55.1 |
| Bacteroides fragilis | 57.0 |
| Bacillus subtilis | 54.3 |
| Aquaspirillum magnetotacticum | 56.5 |
| Neisseria gonorrhoeae | 53.8 |
| Methylobacillus flagellatum | 55.4 |
| Bordetella pertussis | 54.2 |
| Pseudomonas cepacia | 55.4 |
| Escherechia coli | 52.6 |

The amino and carboxy terminal are poorly conserved, although they may have functional significance. Interestingly, the carboxy end is enriched for acidic residues in almost all species analyzed. Although the sequence for Arabidopsis thaliana according to the present invention is more divergent than any of the eubacterial RecA proteins found to date, predicted functional domains of the E. coli protein [see J. Bacteriol. 168:901 (1986)] are largely conserved. Amino acids known to cause recombination deficiency when altered in E. coli RecA [see Biochimie 73:289 (1991); CRC Crit. Rev. Biochem. Mol. Biol 25:415–456 (1990); and J. Bacteriol 171:2415 (1989)] are invariant in the Arabidopsis sequence. However, residues affecting preferentially co-protease activity and/or causing hyper-recombinogenic phenotypes are not so well conserved in the Arabidopsis gene. Since this gene is now located in the nucleus of an eukaryote, it is tempting to speculate that it has acquired a different regulatory system and it is able to evolve independently of LexA.

The plastid genome encodes only a small proportion of the proteins needed for functional chloroplasts [see EMBO J. 5:204.3 (1986)], and it is thought that most genes have been transferred to the nucleus during evolution [see Nucleic Acids Res. 18:65 (1990)]. The base composition and codon usage of these transferred genes have adjusted to reflect their nuclear localization. It has been hypothesized that codon usage is genome specific and provides a basis for species classification comparable to classic systematics [see Nucleic Acids. Res. 8:1893 (1980)]. Several methods [see Nucleic Acids Res 18:65 (1990); Nucleic Acids Res 8:1893 (1980); and FEBS Lett 95:1 (1978)] were used to compare non-homologous sequences to determine the degree of similarity between the sequenced cDNA according to the present invention and several other Arabidopsis, nuclear genes encoding chloroplast proteins. The dinucleotide frequency and base composition (TA/AT ratio, and %G+%C) were not significantly different between the genes examined. However in codon usage distance and the arginine coding ratio, the cloned sequence was indistinguishable from the Arabidopsis genes and clearly different from several eubacterial recA genes as indicated in the following table:

TABLE 1

Codon usage in Arabidopsis thaliana nuclear genes encoding chloroplast proteins and several eubacterial recA genes

| Genes* | CGN/AGR Ratio† | Codon usage distance** |
|---|---|---|
| EPSP Synthase*** | 0.62 | 5.07 |
| Tryptophan Synthetase | 0.47 | 6.28 |
| Acetolactate Synthase | 1.36 | 6.48 |

TABLE 1-continued

Codon usage in *Arabidopsis thaliana* nuclear genes encoding chloroplast proteins and several eubacterial recA genes

| Genes* | CGN/AGR Ratio† | Codon usage distance** |
|---|---|---|
| Cs Gene | 0.33 | 6.42 |
| Rubisco Activase | 0.91 | 6.88 |
| Average ʲ | 0.74 ± 0.41 | 6.22 ± 0.68 |
| Arabidopsis recA | 1.56 | 6.87 |
| Anabaena recA | 5.00 | 10.78 |
| Synechococcus recA | 8.50 | 11.39 |
| Escherichia recA | ∞ ⁱ | 15.82 |

*In plant genes (first 6 listed), sequences corresponding to the mature proteins were used for the analysis (introns and chloroplast transit peptides were excluded). References for the Arabidopsis genes are listed in Plant Mol. Biol. Reporter 9:104 (1991). The Cs gene codes for a chloroplast protein of unknown function. The eubacterial recA genes were obtained from GenBank (release 69).
†Arginine coding ratio, where N = A, C, G, or T and R = A, or G.
**Codon usage distance was determined by a modification of a published procedure [see Nucleic Acids Res 18:65 (1990). Briefly, synonymous codons differing only in their third nucleotides were grouped. Termination codons and single codon groups (methionine and tryptophan) were excluded, leaving 21 codon groups with a total of 59 codons. The relative frequency of different codons in each group was calculated. The overall difference in codon usage between any gene and the Arabidopsis average was computed by a distance algorithm:

$$D(A,X) = \sum_{i=1}^{i=59} |x(i,A) - x(i,\overline{X})|$$

wherein $x(i,A)$ and $x(i,\overline{X})$ are the frequencies of the ith codon in gene A and in the average Arabidopsis nuclear gene encoding a chloroplast protein (determined by pooling the coding sequences of the 5 genes shown).
***5-enolpyruvylshikimate-3-phosphate synthase.
ʲThe Arabidopsis average was calculated from the 5 individual genes shown, and expressed as the mean ± standard deviation. To avoid giving excessive weight to fluctuations in codon usage for rare amino acids, a problem with short proteins, only genes of similar length recA were analyzed.
ⁱ*Escherichia coli* Rec A lacks arginine residues encoded by AGR.
By Spearman's rank correlation coefficient, the CGN/AGR ratio and codon usage distance are correlated with each other (r = 0.88; p < 0.005).

These data suggest that the *Arabidopsis recA* gene has adjusted to reflect its localization in the nuclear genome, clearly diverging from even the more closely related cyanobacterial homologs.

The following example IV depicts the treatment of protoplasts in accordance with the present invention.

EXAMPLE IV

Ten ml of protoplasts ($1 \times 10^6$ protoplasts/ml) in liquid LP* medium [see *In Vitro Cell Dev. Biol.* 25:571 (1989)] were placed in 9-cm Petri dishes. Mitomycin C was added to the desired concentration, and protoplasts were incubated for 12 hours in the dark. Following incubation of the protoplasts with the DNA damaging agent, they were sedimented at 100 xg for 5 minutes. The pellet of intact protoplasts was resuspended in buffer B and reisolated by flotation as described in Example I.

Proteins were then extracted by breaking the protoplast by passage through a 10 μm nylon mesh, collecting the cell fractions (chloroplasts, mitochondria, and non-sedimenting soluble proteins) following centrifugation on a Percoll gradient as described in Example I, and then dissolving these in buffer containing SDS in order to do gel electrophoresis. Alternatively, with the intact chloroplast fraction isolated from the protoplasts, breaking them by resuspension in 10 mM Na Pyrophosphate, centrifuging in the Eppendorf centrifuge to sediment thylakoid and other membranes, collecting the supernatant solution With its proteins, and resuspending the membranes, both of these to be dissolved in SDS buffer and electrophoresed for Western blot analysis.

A reason for Example IV was to determine if DNA damaging agents affect expression of the proteins immunologically related to RecA, and as described, pea protoplasts were incubated with mitomycin C. Mitomycin C is a bifunctional alkylating agent that is activated by reduction and can form interstrand crosslinks [see Science 235:1204 (1987)], presumably requiring a recombinational pathway for repair. The treatment increased the steady state level of the chloroplast cross reacting protein similar in Mr to RecA, suggesting its involvement in DNA repair/recombination (FIG. 1b). The same blot was probed with an antibody against the γ sub-unit of the chloroplast ATP synthetase as a control for the proper loading of the lanes (FIG. 1c).

In summary, the present invention describes a nucleic acid sequence for a gene that encodes for a RecA type of protein in the chloroplasts of higher plants. This is the first time it has ever been found in any higher organisms other than bacteria.

In view of the known roles for RecA in *E. coli*, and induction of the pea enzyme by DNA damage, it is likely that the chloroplast enzyme is also concerned with DNA repair. Although it is not scientifically certain at the present that the Arabidopsis gene can complement a recA-deficient strain of *E. coli*, by using a complementation assay, it has been possible for an isolated a gene from the same Arabidopsis cDNA library, to increase the survival of a mutant (phr", uvB", recA") *E. coli* strain exposed to UV. However, its DNA sequence is quite different from the one isolated by hybridization with recA probe according to the present invention. In view of the complex pathways for DNA repair in bacteria [see *Ann. Rev. Genet.* 21:179 (1987)] it is likely that a number of proteins will be needed to interact with RecA in chloroplasts as well.

The recA gene according to the present invention has a number of uses. For example, by removing the 5' end of the gene, that is the portion of the gone which codes for a "transit peptide" portion of the protein that directs the final product into chloroplasts, this transit peptide could be replaced by an amino acid sequence that directs completed proteins to enter the nucleus.

In order to understand the importance of such "redirection"', one must be aware of the function of RecA protein in homologous recombination as found in prokaryotes. Genetic engineering has been vastly more efficient in prokaryotes than in eukaryotes (with the exception of yeast), because in bacteria and yeast the exogenous pieces of DNA are integrated into the chromosome by homologous recombination, a procedure not available in higher plants. By introducing the RecA protein, now found only in chloroplasts, into the nuclei of higher plants, it should be possible to increase the frequency of homologous recombination in the chromosomal genes of these higher plants. There are several potential advantages of using the recA gone according to the present invention for this purpose. For example, while the gene may be related to prokaryotic progenitors, the gene has been present and functioning in higher plants, and so its codon usage (and other housekeeping aspects) are already adapted to the nuclear environment; the same would certainly not be true of a recA gene taken from a bacteria.

Thus, while We have illustrated and described the preferred embodiment of our invention, it is to be understood that this invention is capable of variation and modification, and we therefore do not wish to be limited to the precise terms set forth, but desire to avail ourselves of such changes and alterations which may be made for adapting the invention to various usages and conditions. Such changes and alterations to the present invention include, without limitation, single base substitutions, and deletions, insertions or translations of the DNA sequences presented herein providing that such alterations do not significantly affect the properties of the altered sequence from that of the cDNA sequences given above. For example, in specific instances it may be more advantageous to insert or delete certain nucleic acids within the sequence give in accordance with the present invention, or to utilize a portion or fragment of the nucleic acid sequence according to the present invention without significantly altering the function of the sequence or resulting expressed peptide. In additions in specific instances it may also be advantageous to insert or delete certain amino acids Within the sequence given in accordance with the present invention, or to utilize a portion or fragment of the amino acid sequence according to the present invention without significantly altering its function. Accordingly, such changes and alterations are properly intended to be within the full range of equivalents, and therefore within the purview of the following claims.

A description of the specific nucleic and amino acid sequences described in the present invention are provided in the following sequence listing:

Having thus described our invention and the manner and a process of making and using it in such full, clear, concise and exact terms so as to enable any person skilled in the art to which it pertains, or with which it is most nearly connected, to make and use the same;

What is claimed is:

1. An isolated nucleic acid molecule encoding a RecA-like protein of *Arabidopsis thaliana* comprising the nucleotide sequence set forth as SEQ ID NO:3.

2. An isolated nucleic acid molecule encoding a RecA-like protein of *Arabidopsis thaliana* wherein said nucleic acid molecule encodes the amino acid sequence set forth as SEQ ID NO:4.

\* \* \* \* \*